(12) United States Patent
Fetzer

(10) Patent No.: US 10,515,448 B2
(45) Date of Patent: Dec. 24, 2019

(54) HANDPRINT ANALYSIS TO PREDICT GENETICALLY BASED TRAITS

(71) Applicant: International Business Machines Corporation, Armonk, NY (US)

(72) Inventor: Stephanie A. Fetzer, Wilmington, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/270,832

(22) Filed: Sep. 20, 2016

(65) Prior Publication Data

US 2018/0082419 A1    Mar. 22, 2018

(51) Int. Cl.

| | |
|---|---|
| *G06T 7/00* | (2017.01) |
| *G06N 20/00* | (2019.01) |
| *G06K 9/00* | (2006.01) |
| *G06K 9/62* | (2006.01) |
| *G16B 20/00* | (2019.01) |
| *G16H 30/40* | (2018.01) |
| *G16H 50/20* | (2018.01) |
| *G06K 9/46* | (2006.01) |
| *G16B 40/30* | (2019.01) |

(Continued)

(52) U.S. Cl.
CPC ........ *G06T 7/0012* (2013.01); *G06K 9/00382* (2013.01); *G06K 9/6262* (2013.01); *G06N 20/00* (2019.01); *G16B 20/00* (2019.02); *G16H 30/40* (2018.01); *G16H 50/20* (2018.01); *G06K 9/4671* (2013.01); *G06T 2207/20081* (2013.01); *G06T 2207/30004* (2013.01); *G16B 40/10* (2019.02); *G16B 40/20* (2019.02); *G16B 40/30* (2019.02)

(58) Field of Classification Search
None
See application file for complete search history.

(56) References Cited

U.S. PATENT DOCUMENTS

| | | | |
|---|---|---|---|
| 7,689,016 B2 | 3/2010 | Stoecker et al. | |
| 8,391,590 B2 * | 3/2013 | Yalla | G06K 9/00 340/5.53 |
| 8,504,343 B2 | 8/2013 | Chawla et al. | |

(Continued)

FOREIGN PATENT DOCUMENTS

CN    104131607 A    11/2014

OTHER PUBLICATIONS

Devi, M. Parvathi, et al. "Skin Carvings: Predictive Diagnosis in Modern Era." (2015), IJSS Case Reports & Reviews, pp. 75-80.*

(Continued)

*Primary Examiner* — Samah A Beg
(74) *Attorney, Agent, or Firm* — Patterson + Sheridan, LLP

(57) ABSTRACT

The present disclosure relates to techniques for predicting a genetically based trait using handprints. In one embodiment, a method generally includes receiving a digital image of a person's handprint. A computing device extracts features from the digital image using at least one feature-extraction technique and inputs the features into a machine-learning model trained to predict at least one genetically based trait when such features are received as input. The machine-learning model predicts whether the user has one or more genetically based traits based on the values of the features. The computing device then sends the prediction to an application that presents the prediction to the user.

20 Claims, 7 Drawing Sheets

(51) Int. Cl.
    *G16B 40/20* (2019.01)
    *G16B 40/10* (2019.01)

(56) References Cited

U.S. PATENT DOCUMENTS

| | | | | |
|---|---|---|---|---|
| 9,292,916 | B2 | 3/2016 | Rowe | |
| 2005/0201596 | A1* | 9/2005 | Hwang | G06K 9/0008 382/124 |
| 2006/0147096 | A1* | 7/2006 | Lee | G06K 9/00067 382/124 |
| 2009/0281414 | A1* | 11/2009 | Feldman | A61B 5/04005 600/409 |
| 2011/0025827 | A1* | 2/2011 | Shpunt | H04N 13/0239 348/47 |
| 2015/0347805 | A1* | 12/2015 | McNulty | G06K 9/00033 382/124 |
| 2016/0022151 | A1 | 1/2016 | Davis | |
| 2017/0091526 | A1* | 3/2017 | John Archibald | G06K 9/00013 |
| 2018/0089483 | A1* | 3/2018 | Norimatsu | G06T 7/00 |

OTHER PUBLICATIONS

Johnson, A. E. (1997). Spin-images: a representation for 3-D surface matching (Doctoral dissertation, Carnegie Mellon University). (Year: 1997).*

Stein, F., & Medioni, G. (1992). Structural indexing: Efficient 3-D object recognition. IEEE Transactions on Pattern Analysis and Machine Intelligence, 14(2), 125-145.*

Chen, H., & Bhanu, B. (2007). 3D free-form object recognition in range images using local surface patches. Pattern Recognition Letters, 28(10), 1252-1262.*

Stein, F., & Medioni, G. (1992). Structural indexing: Efficient 3-D object recognition. IEEE Transactions on Pattern Analysis and Machine Intelligence, 14(2), 125-145. (Year: 1992).*

Chen, H., & Bhanu, B. (2007). 3D free-form object recognition in range images using local surface patches. Pattern Recognition Letters, 28(10), 1252-1262. (Year: 2007).*

Yu, Lei, and Huan Liu. "Feature selection for high-dimensional data: A fast correlation-based filter solution." Proceedings of the 20th international conference on machine learning (ICML-03). 2003. (Year: 2003).*

Chintamani, et al., "Qualitative and quantitative dermatoglyphic traits in patients with breast ; cancer: A prospective clinical study", 200BioMed Central; cancer: A prospective clinical study, 2007, accessed May 22, 2016.

A. Sanchez Cascos, "Fingerprint Patterns in Congenital Heart Disease," 1964, pp. 1-4.

Prabhakar et ak., "FingerCode: A Filterbank for Fingerprint Representation and Matching," 1999, pp. 1-8.

Zhang, et al., "Detection of microaneurysms using multi-scale correlation coefficients," Pattern Recognition, v. 43, n. 6, Jun. 2010, 2237-2248, pp. 1-12.

McBride, "Disease Inheritance and Race Determination by Fingerprints," SCAFO, pp. 1-3.

NIST Biometric Image Software, NBIS, Release 5.0.0, http://www.nist.gov/itl/iad/ig/nbis.cfm, created 2010, last updated Mar. 4, 2015, pp. 1-6.

"Palm Reading Perspectives", https://palmreadingperspectives.wordpress.com/2011/06/20/fingerprints-reveal-clues-about-sexe-race-diet-lifestyle-disease/, pp. 1-3.

The Ability to Predict Disease May be at Your Fintertips, http://www.dadamo.com/txt/index.pl?1041, reviewed/revised Mar. 3, 2015.

Weinreb, MD, Herman J., "Fingerprint Pattersn in Alzheimer's Disease," Arch Neurol—vol. 42, Jan. 1985, pp. 1-5.

* cited by examiner

HANDPRINT ANALYSIS TO PREDICT GENETICALLY BASED TRAITS

BACKGROUND

Variant alleles and other genetic traits cause or influence human diseases. The Online Mendelian Inheritance in Man (OMIM) compendium of human genes and genetic disorders, for example, lists thousands of alleles that have been linked to human diseases. Both well-known diseases such as diabetes and lesser-known diseases such as Von Willebrand disease and Creutzfeldt-Jakob disease can have genetic causes.

Many companies now offer genetic testing to screen for genetically based diseases. This genetic testing can be valuable diagnostic tool, especially for patients that experience symptoms that can be caused by many different diseases. For example, if a patient experiences symptoms that could be caused by multiple sclerosis or fibromyalgia, a genetic test may help a doctor diagnose the cause correctly. The doctor can then prescribe an appropriate treatment based on the diagnosis.

Genetic testing typically involves a multi-step process. First, a blood sample (or tissue) is sent to a laboratory. Laboratory technicians isolate the DNA in the sample. Lab technicians then typically apply polymerase chain reaction (PCR) techniques to amplify the isolated DNA. The amplified DNA is sequenced. The DNA sequence is then compared to allele sequences known to be associated with certain diseases.

In general, it takes at least two weeks for a patient to receive the results of a genetic test from a commercial laboratory or research center. The price for a genetic test typically ranges from about $100 to $2,000, depending on the nature and complexity of the test. Tests for genetic attributes linked to over 2,500 diseases are currently commercially available.

SUMMARY

One embodiment disclosed herein includes a method for diagnosing a genetically based trait using a handprint. The method generally includes receiving a digital image of a user's handprint. A computing device extracts features from the digital handprint using at least one feature-extraction technique and inputs the features into a machine-learning model. The machine-learning model, having been trained beforehand using training data, predicts whether the user has a genetically based trait based on the features. The computing device then sends the prediction to an application that presents the prediction to the user.

Another embodiment includes non-transitory computer-readable storage medium containing instructions that, when executed by one or more processors, perform an operation for diagnosing a genetically based trait using a handprint. The operation generally includes receiving a digital image of a user's handprint. A computing device extracts features from the digital handprint using at least one feature-extraction technique and inputs the features into a machine-learning model. The machine-learning model, having been trained beforehand using training data, predicts whether the user has a genetically based trait based on the features. The computing device then sends the prediction to an application that presents the prediction to the user.

Still another embodiment includes one or more processors and memory storing one or more applications that, when executed on the one or more processors, perform an operation for diagnosing a genetically based trait using a handprint. The operation generally includes receiving a digital image of a user's handprint. A computing device extracts features from the digital handprint using at least one feature-extraction technique and inputs the features into a machine-learning model. The machine-learning model, having been trained beforehand using training data, predicts whether the user has a genetically based trait based on the features. The computing device then sends the prediction to an application that presents the prediction to the user.

DETAILED DESCRIPTION

Embodiments presented herein provide techniques for predicting genetically based traits using digital images of handprints. Labeled training data for a machine-learning model is generated using genetic testing results for people whose handprints have been digitally captured. The machine-learning model is trained using the training data. Through the training process, the machine-learning model identifies predictive relationships between handprint attributes and genetic traits and tunes parameters to reflect those relationships.

The machine-learning model is then made available to an application through a network connection. The application sends an image of a person's handprint to the computing system. The computing system extracts features from the image evaluated by the machine learning model. The machine-learning model correlates the features with one or more genetic traits. The computing system sends a message to the application providing the prediction. In this manner, the computing system can provide the prediction relatively quickly and inexpensively. The person does not have to endure any invasive or uncomfortable procedure to provide a deoxyribonucleic acid (DNA) sample, pay a large fee, or wait for weeks to receive test results.

Figure 1:
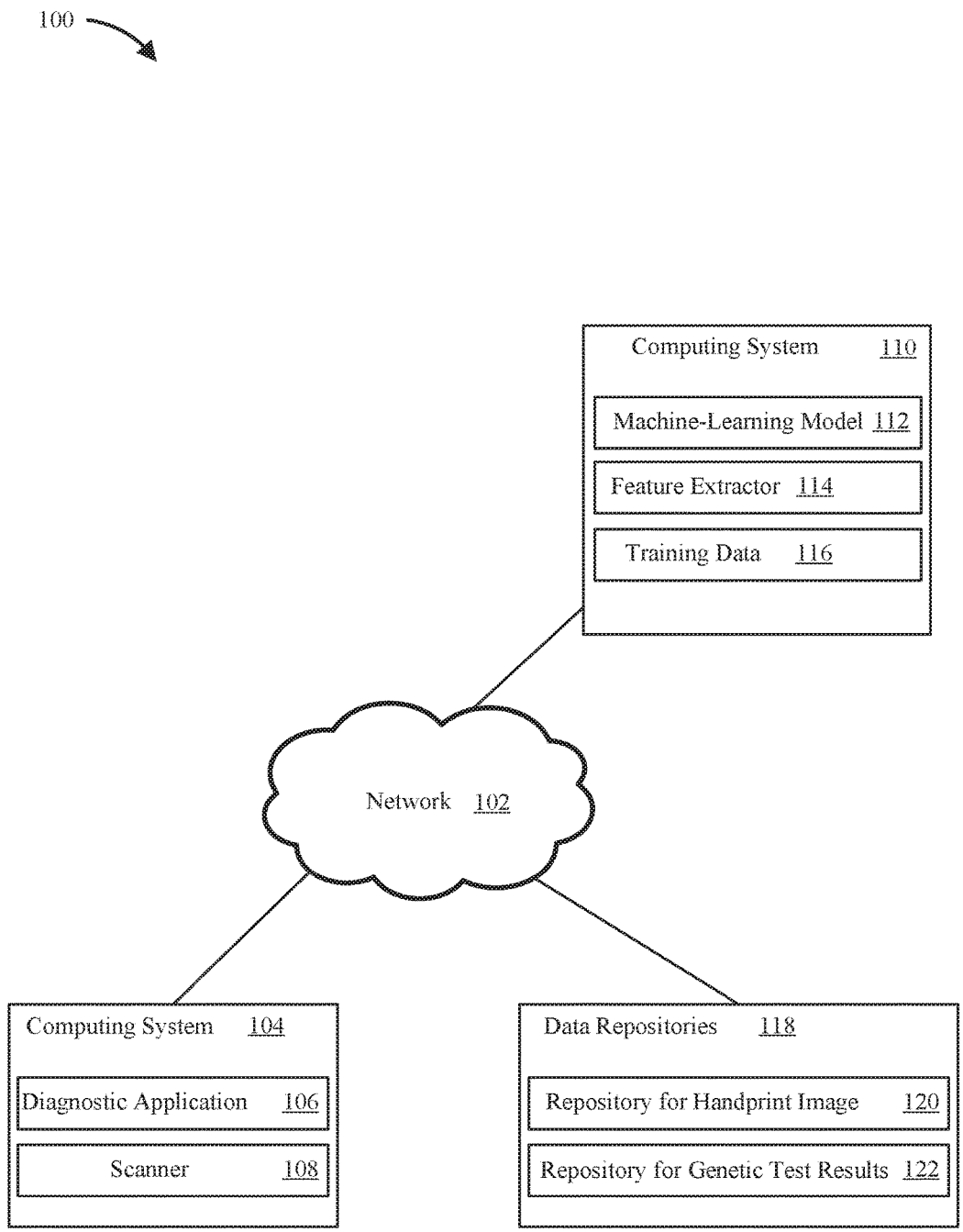
FIG. 1 illustrates a computing environment, according to one embodiment.

FIG. 1 illustrates a computing environment 100 in which techniques of the present disclosure are applied, according to one embodiment. As shown, the computing environment 100 that can evaluate handprint features to predict genetic traits includes a computing system 110 hosting a machine-learning model 112, a feature extractor 114, and training data 116. The machine-learning model 112 is trained to make genotype predictions based on handprints using the training data 116.

The computing system 110 derives the training data 116 from the data repositories 118. More specifically, the computing system 110 extracts features of the training data 116 from the repository for handprint images 120 and derives labels for the training data 116 from the repository for genetic test results 122.

The computing system 104 includes a scanner 108 and a diagnostic application 106. The scanner 108 captures a digital image of a person's handprint for the diagnostic application 106. The diagnostic application 106 sends the digital image to the computing system 110 via the network 102.

The feature extractor 114 extracts features from the digital image and provides the features as input to the machine-learning model 112. The machine-learning model 112 predicts the person's genotype based on the features provided by the feature extractor 114 for the digital image of the person's hand. The computing system 110 sends the person's predicted genotype, as determined by the machine-learning model 112, to the diagnostic application 106 via the network 102. The diagnostic application 106 provides the predicted genotype to the person as a diagnosis.

Figure 2:
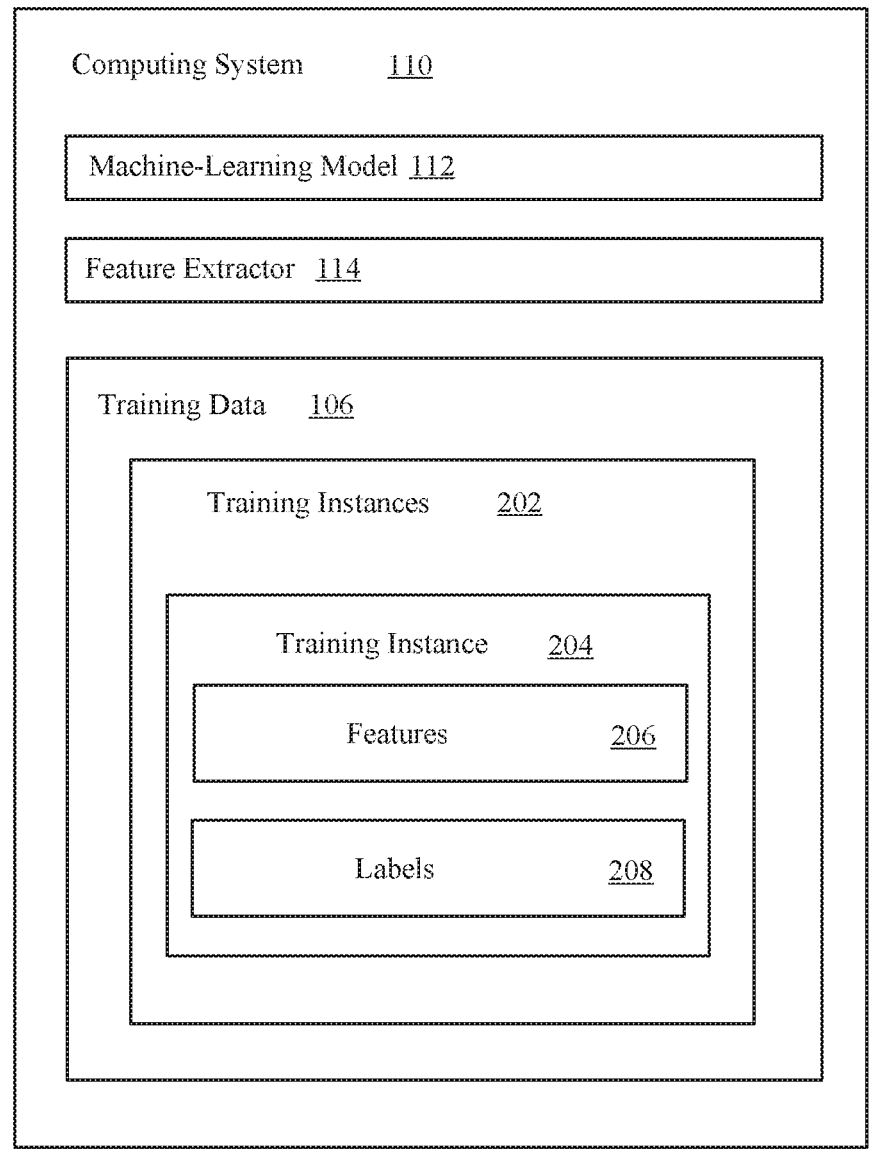
FIG. 2 illustrates a more detailed view of a computing system and training data, according to one embodiment.

FIG. 2 illustrates a more detailed view of the computing system 110 and the training data 106, according to one embodiment. As shown, the computing system 110 includes the machine-learning model 112, the feature extractor 114, and the training data 106. The training data 106 includes training instances 202. Each training instance in the training instances 202 corresponds to a person for whom both handprint data and genotypic data are available.

Training instance 204 is provided as an example. As shown, training instance 204 includes features 206. The term "feature" refers to an attribute that quantifies or categorizes some aspect of a handprint image. The feature extractor 114 derives the features 206 from a digital image of a handprint for a person the training instance 204 represents. The labels 208 are known genotypes or phenotypes of the person the training instance 204 represents. The machine learning model 112 is trained to predict the labels 208 based on the features 206.

Figure 3:
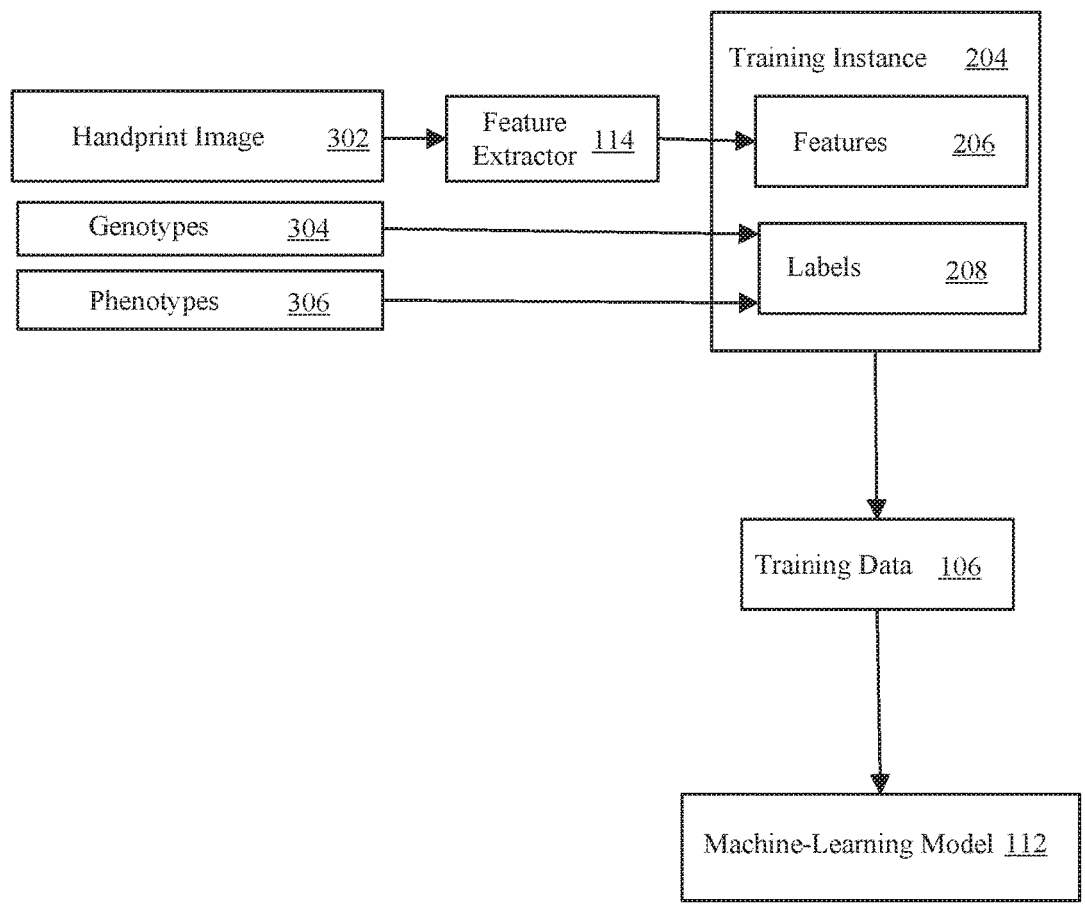
FIG. 3 illustrates an example process by which a training instance can be created and used to train a machine-learning model, according to one embodiment.

In one embodiment, the handprint image may be a two-dimensional (2D) image such as a digitized version of an inked handprint. In another embodiment, the handprint image may be capture three-dimensional (3D) aspects of the hand. In one example, a person's hand may be scanned to produce a 3D model of the hand, such as a stereolithography (STL) file, that serves as the handprint image. FIG. 3 illustrates an example process for creating the training instance 204 and training the machine-learning model 112, according to one embodiment. As shown, a handprint image 302 depicting a handprint of a person, the genotypes 304 of the person, and the phenotypes 306 of the person are used to generate the training instance 204. The feature extractor 114 receives the handprint image 302 and extracts features 206. The genotypes 304 and the phenotypes 306 are encoded as the labels 208.

The training instance 204 is added to the training data 106. The training data 106 also includes other training instances. The machine-learning model 112 is then trained using the training data 106 to receive features as input and to predict labels based on the features. The labels can indicate genetically based traits such as genotypes, phenotypes, single-nucleotide polymorphisms (SNPs), deletions, an insertions, translocations, numbers of homologous chromosomes, DNA methylation patterns, or the presence of certain alleles.

Figure 4:
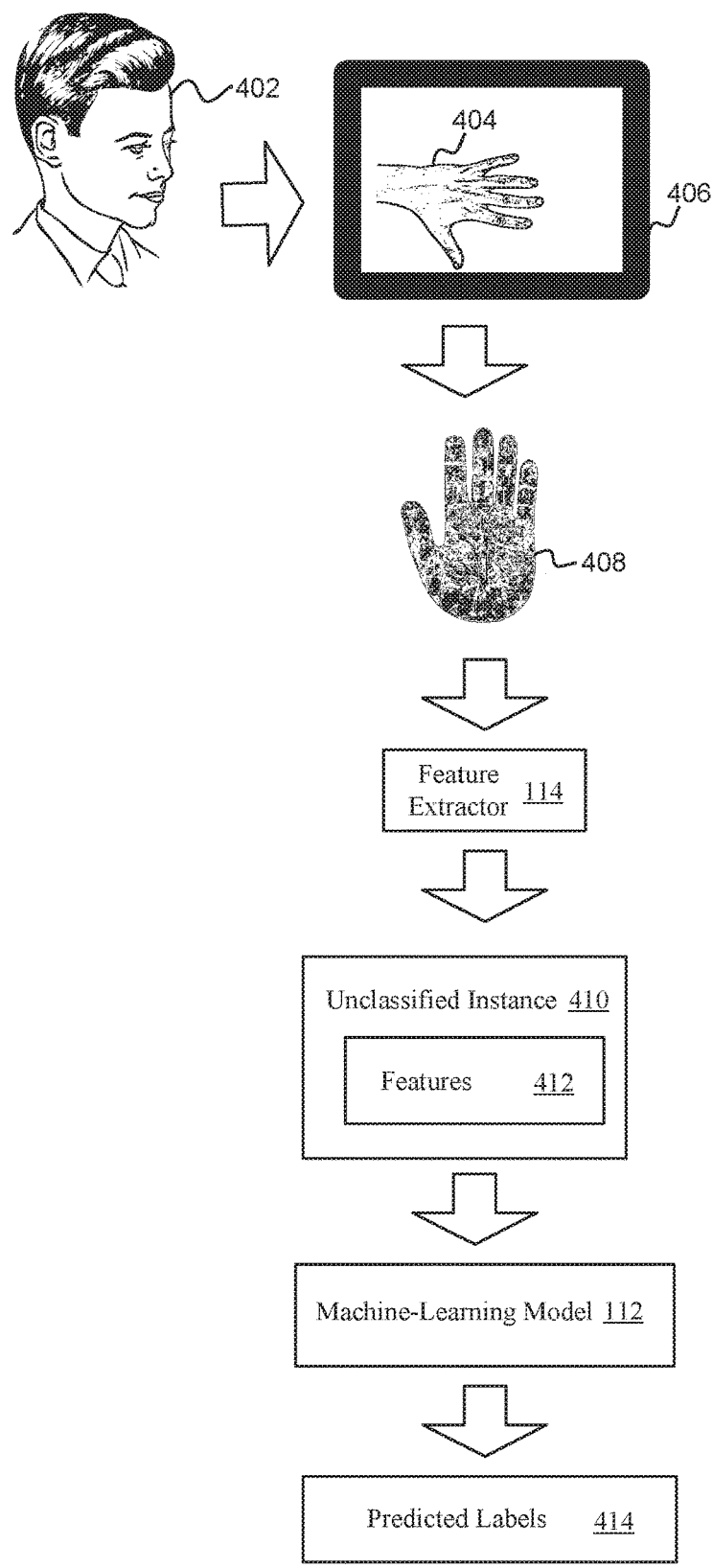
FIG. 4 illustrates an example process of diagnosing a genotype or phenotype of a person based on a handprint, according to one embodiment.

FIG. 4 illustrates an example process of diagnosing a genotype or phenotype of a person 402 based on a handprint, according to one embodiment. The person 402 captures a digital image 408 of at least the palm side of hand 404 of person 402 using scanner 406. The digital image may also include 3D aspects of the hand 404 that extend beyond the palm side, depending on the capabilities of the scanner 406. The feature extractor 114 extracts features 412 from the digital image 408. The features 412 are included in an unclassified instance 410 for the machine learning model 112. The machine-learning model 112 receives the unclassified instance 410 as input. Based on the features 412, the machine-learning model outputs predicted labels 414. The predicted labels 414 are predicted genotypes or phenotypes for the person 402.

There are many different types of inductive and transductive machine-learning models that can be used for the machine-learning model 112. Examples of machine-learning models include adsorption models, neural networks, support vector machines, radial basis functions, Bayesian belief networks, association-rule models, decision trees, instance-based models (e.g., k-NN), regression models, Hopfield networks, deep belief networks, and Q-learning models.

Many configurations and parameter combinations may be possible for a given type of machine-learning model. With a neural network, for example, the number of hidden layers, the number of hidden nodes in each layer, and the existence of recurrence relationships between layers can vary. True gradient descent or stochastic gradient descent may be used in the process of tuning weights. The learning rate parameter, which partially determines how much each weight may be adjusted at each step, may be varied. Input features may be normalized. Other parameters that are known in the art, such as momentum, may also be applied to improve neural network performance. In another example, decision trees can be constructed using a variety of approaches. Some non-limiting examples include the iterative dichotomiser 3 (ID3), Classification and Regression Tree (CART), and CHi-squared Automatic Interaction Detection (CHAID) methods. These methods may use one or more different metrics to determine the order in which attribute values are examined in decision trees. Some non-limiting examples of such metrics include information gain and Gini impurity. In addition, pruning methods may be applied to improve decision tree performance. Some non-limiting examples of pruning techniques include reduced error pruning, cost complexity pruning, and alpha-beta pruning.

Furthermore, individual machine learning models can be combined to form an ensemble machine-learning model. An ensemble machine-learning model may be homogenous (i.e., using multiple member models of the same type) or non-homogenous (i.e., using multiple member models of different types). Individual machine-learning models within an ensemble may all be trained using the same training data or may be trained using overlapping or non-overlapping subsets randomly selected from a larger set of training data.

Figure 5:
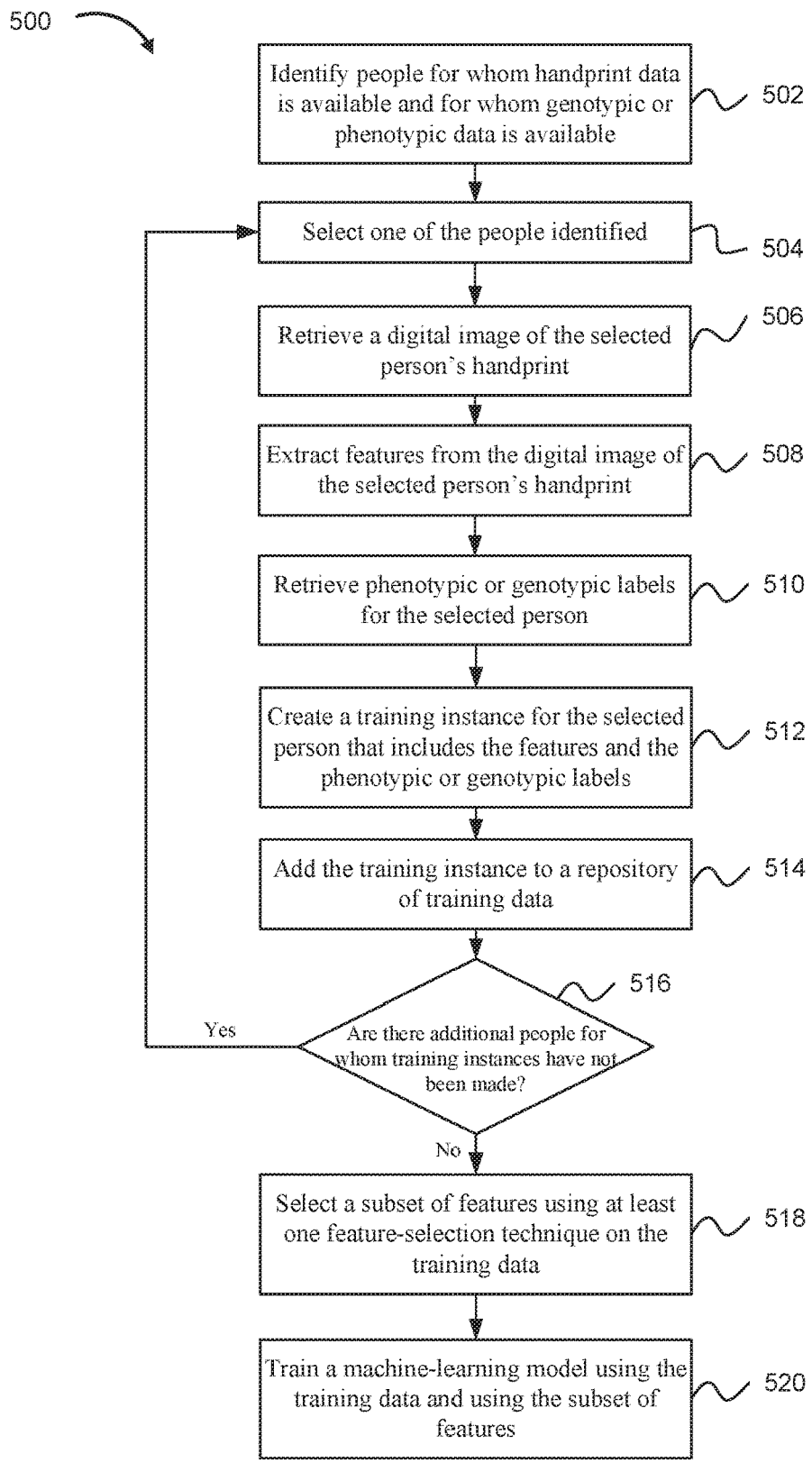
FIG. 5 illustrates a method for developing a machine-learning model that predicts genotypes or phenotypes based on handprint data, according to one embodiment.

FIG. 5 illustrates a method 500 for creating a machine-learning model that predicts genotypes or phenotypes based on handprint data, according to one embodiment. The method 500 can be implemented as a method or can be executed as instructions on a machine by one or more processors, where the instructions are included on at least one computer-readable storage medium (e.g., a transitory or non-transitory computer-readable storage medium).

At step 502, the trainer application identifies people for whom both handprint data and genotypic or phenotypic data are available. In order to do so, the trainer application can use many different approaches. If a database that stores both handprints and genotypes for people is available, the trainer application can simply query the database for a list of all people for whom handprint images and genotypes are stored. Otherwise, or if more data is desired, the trainer application can compare or cross-reference names in a database of handprint images with names in a database of genotypic data. The trainer application can then add names that have entries in both databases to the list.

At step 504, the trainer application selects one of the people identified in step 502. At step 506, the trainer application retrieves a digital image of the selected person's handprint. At step 508, a feature extractor extracts features from the digital image of the selected person's handprint using at least one feature-extraction technique.

At step 510, the trainer application retrieves phenotypic or genotypic labels for the selected person (e.g., from the database of genotypic data). At step 512, the trainer application creates a training instance for the selected person that includes the features and the phenotypic or genotypic labels. At step 514, the trainer application adds the training instance to a repository of training data. One example of a common file format that is used to store training data for machine-learning models is the attribute-relation file format (ARFF), though other formats may be used.

At step 516, the trainer application determines whether there are additional people for whom training instances have not yet been made. If there are, steps 504-514 are repeated for each of the additional people. Otherwise, the trainer application proceeds to step 518.

At step 518, the trainer application selects a subset of features using at least one feature-selection technique on the training data. Some feature-selection techniques that can be applied include the Las Vegas Filter (LVF), Las Vegas Incremental (LVI), Relief, Sequential Forward Generation (SFG), Sequential Backward Generation (SBG), Sequential Floating Forward Search (SFFS), Focus, Branch and Bound (B & B), and Quick Branch and Bound (QB&B) techniques.

There are several reasons why it is useful to select a subset of features before training a machine-learning model. For example, some of the features extracted at step 508 may not be appreciably correlated to label quantities that the machine-learning model is designed to predict. Irrelevant features can cause overfitting some machine-learning models. In addition, one feature may be so closely correlated with another feature that it would be redundant to use both for training. Furthermore, redundant features can blunt the accuracy of some distance metrics used in instance-based models. Also, when irrelevant or redundant features are present in training data, most machine-learning models take longer to train.

In general, the number of features included in the subset should be small relative to the total number of training instances in the training data. In some embodiments, the number of features selected for the subset can be at least two orders of magnitude smaller than the number of training instances in the training data.

At step 520, the trainer application trains a machine-learning model using the training data and using the subset of features. When the training process is complete, the machine-learning model is ready to predict phenotypic or genotypic labels based on features extracted from handprint images.

Figure 6:
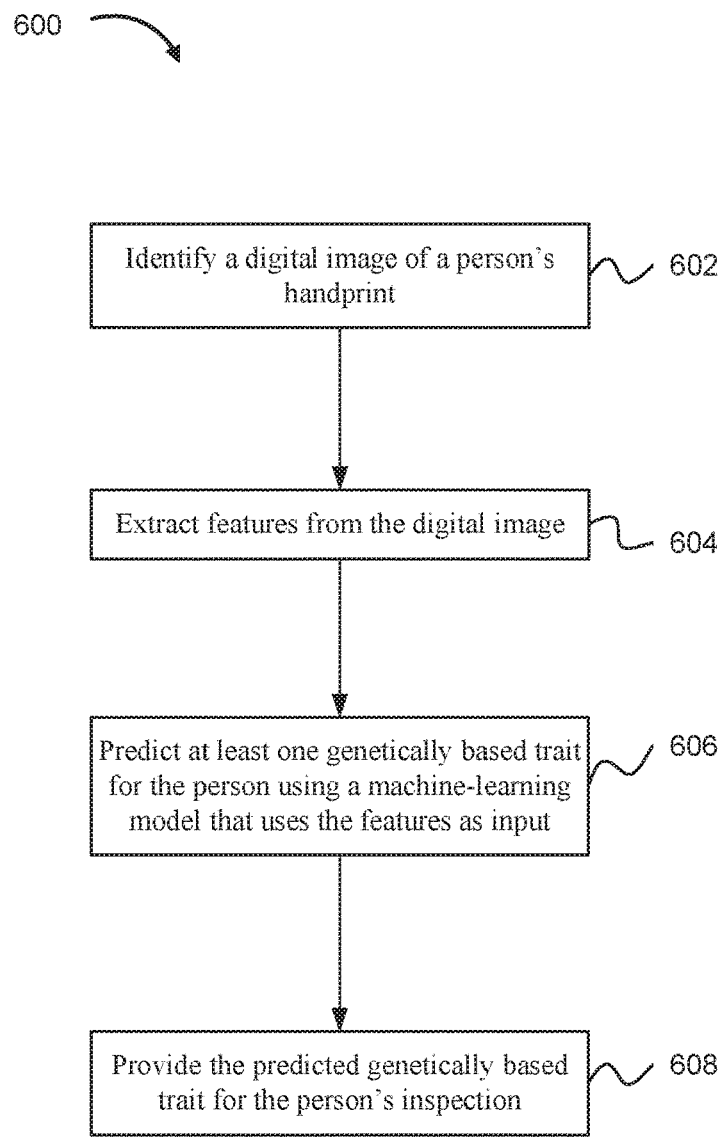
FIG. 6 illustrates a method for predicting one or more genetically based traits of a person based on the person's handprint.

FIG. 6 illustrates a method 600 for predicting genetically based traits from a handprint, according to one embodiment. At step 602, a diagnostic application identifies a digital image of a person's handprint. In general, a scanning device captures the digital image of the person's handprint. The scanning device may be a flatbed scanner, a 3D scanner, or some other type of scanner (including a digital camera used as a scanner). The scanning device may capture the image directly from the person's hand. Alternatively, the scanning device may capture the image by scanning a paper that has an ink print that was formed by pressing the hand against an ink pad and pressing the hand against paper.

At step 604, a feature extractor extracts features from the digital image using at least one feature-extraction technique. Some examples of computer-vision methods for feature extraction and detection that may be applied at step 604 include Scale-Invariant Feature Transform (SIFT), Speeded Up Robust Features (SURF), Oriented features from accelerated segment test and Rotated Binary robust independent elementary features (ORB), Smallest Univalue Segment Assimilating Nucleus (SUSAN), Maximally Stable Extremal Regions (MSER), and Principal Curvature-based Region Detector (PCBR). Some types of features that can be detected and quantified include edges, corners, interest points, blobs, regions of interest, and ridges. Other features, such as locations and diameters of sweat pores, directional variance of a ridge-orientation field, and other geometric characteristics of ridges, loops, whorls, or arches may also be extracted. If the digital image incorporates 3D aspects of the hand, the feature extractor may also detect features such as Medioni splashes, Johnson & Herbert Spin images, and curvature histograms.

At step 606, the diagnostic application predicts at least one genetically based trait for the person using a machine-learning model that uses the features as input. At step 608, the diagnostic application provides the predicted genetically based trait for the person's inspection. Optionally, in some embodiments, the predicted genetically based traits may include epigenetic attributes (e.g., DNA methylation patterns).

In one embodiment, the diagnostic application can also compare a predicted genetically based trait to a list that cross-references genetically based traits to diseases (e.g., genetic disorders). In some cases, the diagnostic application can make an immediate diagnosis by comparing the predicted trait to the list. In one example, if the predicted trait includes the single-nucleotide polymorphism (SNP) for sickle-cell anemia, the diagnostic application can also provide a diagnosis of sickle-cell anemia for the user's inspection. Other examples of diseases and conditions that can be diagnosed directly from predicted genetically based traits include Turner syndrome (e.g., when there is only one copy of chromosome 23), Down's syndrome (e.g., when there are three copies of the long arm of chromosome 21), and autosomal recessive conditions such as Phenylketonuria.

In other examples, the diagnostic application may diagnose a person as having an elevated risk of developing a certain disease based on the predicted trait. If the predicted trait includes the BRCA1 gene, for example, the diagnostic application may provide a diagnosis indicating that the person has an elevated risk of developing breast cancer. Other examples of diseases and conditions for which elevated risk levels can be diagnosed based on predicted genetically based traits include Huntington's disease (e.g., when there are too many triplet repeats in the gene coding for a specific protein) and leukemia (e.g., when the Philadelphia chromosome is present).

Figure 7:
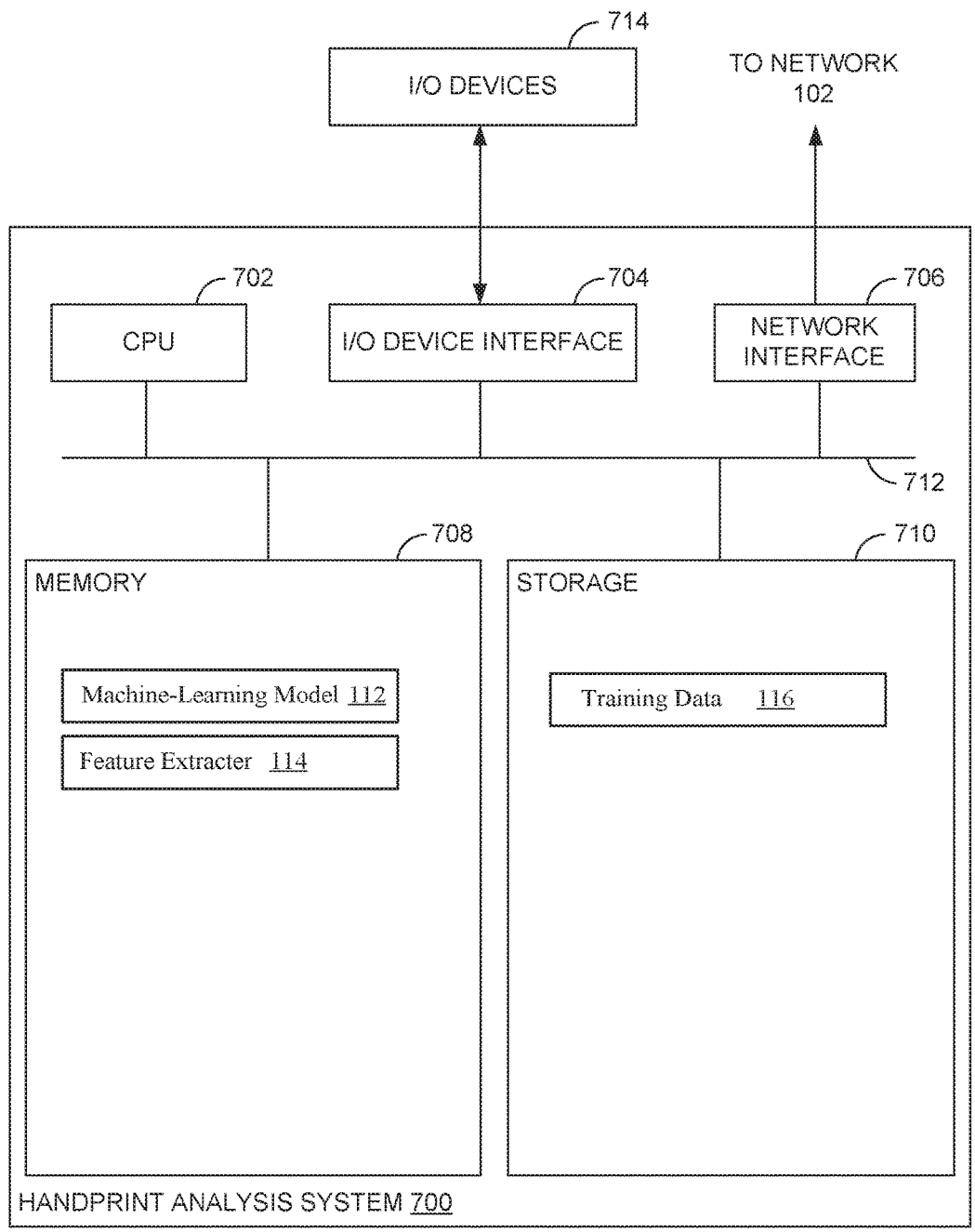
FIG. 7 illustrates an example handprint analysis system that predicts genotypes based on handprints, according to one embodiment.

FIG. 7 illustrates an example handprint analysis system 700 that predicts genotypes based on handprints, according to one embodiment. As shown, the handprint analysis system 700 includes, a central processing unit (CPU) 702 input/output (I/O) device interfaces 704 connecting various I/O devices 714 (e.g., keyboards, displays, mouse devices, pen input, etc.) to the handprint analysis system 700, network interface 706, a memory 708, storage 710, and an interconnect 712.

CPU 702 may retrieve and execute programming instructions stored in the memory 708. Similarly, the CPU 702 may retrieve and store application data residing in the memory 708. The interconnect 712 transmits programming instructions and application data, among the CPU 702, I/O device interface 704, network interface 706, memory 708, and storage 710. CPU 702 can represent a single CPU, multiple CPUs, a single CPU having multiple processing cores, and the like. Additionally, the memory 706 represents random access memory. Furthermore, the storage 710 may be a disk drive. Although shown as a single unit, the storage 710 may be a combination of fixed and/or removable storage devices, such as fixed disc drives, removable memory cards or optical storage, network attached storage (NAS), or a storage area-network (SAN).

As shown, memory 708 includes a machine-learning model 112 and feature extractor 114. As shown, storage 710 includes training data 116. The machine-learning model is trained to predict genetically based traits using features extracted from handprint images as input. The feature extractor 114 can extract features from an image of a person's handprint and provide the extracted features to the machine-learning model 112. The machine-learning model 112 can predict a genetically based trait for the person and send the prediction via the network interface 706.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A method for predicting a genetic trait of an individual based on a hand of that individual, the method comprising:
   receiving a digital image of the hand created from scan data captured by a three-dimensional (3D) scanner, wherein the digital image is a three-dimensional (3D) model of the hand that captures a palm side of the hand and additional 3D aspects of the hand that extend beyond the palm side of the hand;
   extracting, from the digital image via a processor applying at least one computer-vision technique for feature extraction, a collection of features characterizing three-dimensional (3D) aspects of the hand, wherein the collection of features includes directional variance of a ridge-orientation field;
   inputting the extracted features into a machine-learning model executed by the processor to make a prediction of whether the individual has a genetic trait, wherein the machine-learning model is trained to predict the genetic trait based on the collection of features, and wherein the prediction includes predicting whether the individual has: (i) a first genotype, (ii) a single-nucleotide polymorphism, (ii) a deletion, (iii) an insertion, (iv) a translocation, (v) a number of homologous chromosomes, (vi) a first deoxyribonucleic acid methylation pattern, and (vii) a presence of one or more alleles; and
   inputting the extracted features into the machine-learning model to make a prediction of a phenotype of the individual.

2. The method of claim 1, further comprising:
   generating a set of training instances, wherein each training instance includes an image of a respective hand and indicates one or more genetic characteristics; and
   training the machine-learning model using the set of training instances.

3. The method of claim 2, further comprising:
   extracting, from each respective image of a respective training instance, a plurality of features, wherein the plurality of features includes at least a first feature;
   identifying a feature subset from the plurality of features for the machine-learning model using a feature-selection technique, wherein the feature subset excludes the first feature and wherein the feature subset includes a number of features that is at least two orders of magnitude smaller than a number of training instances in the set of training instances; and
   training the machine-learning model to predict the genetic trait based on the feature subset.

4. The method of claim 3, wherein the first feature is excluded from the feature subset based on determining either (i) that a level of correlation between the first feature and the one or more genetic characteristics is below a predefined threshold, or (ii) that a level of correlation between the first feature and at least one other feature in the plurality of features exceeds a predefined threshold.

5. The method of claim 1, wherein the collection of features includes geometric characteristics of ridges, loops, whorls, or arches found in a handprint of the hand.

6. The method of claim 1, wherein extracting the collection of features includes applying each of: Scale-Invariant Feature Transform (SIFT), Speeded Up Robust Features (SURF), Oriented features from accelerated segment test and Rotated Binary robust independent elementary features (ORB), Smallest Univalue Segment Assimilating Nucleus (SUSAN), Maximally Stable Extremal Regions (MSER), and Principal Curvature-based Region Detector (PCBR).

7. The method of claim 1, further comprising:
comparing the prediction to a list that cross-references genetic traits to genetic disorders; and
diagnosing the individual as having a genetic disorder based on the comparison.

8. The method of claim 1, further comprising diagnosing the individual as having an elevated risk of developing a disease based on the prediction.

9. The method of claim 1, wherein the collection of features includes one or more attributes of sweat pores of the hand, including (i) a location of one or more sweat pores, and (ii) a diameter of one or more sweat pores.

10. A non-transitory computer-readable storage medium containing instructions that, when executed by one or more processors, perform an operation for diagnosing a genetically based trait of an individual based on a hand, the operation comprising:
receiving a digital image of the hand created from scan data captured by a three-dimensional (3D) scanner, wherein the digital image is a three-dimensional (3D) model of the hand that captures a palm side of the hand and additional 3D aspects of the hand that extend beyond the palm side of the hand;
extracting, from the digital image via a processor applying at least one computer-vision technique for feature extraction, a collection of features characterizing three-dimensional (3D) aspects of the hand, wherein the collection of features includes directional variance of a ridge-orientation field;
inputting the extracted features into a machine-learning model executed by the processor to make a prediction of whether the individual has a genetic trait, wherein the machine-learning model is trained to predict the genetic trait based on the collection of features, and wherein the prediction includes predicting whether the individual has: (i) a first genotype, (ii) a single-nucleotide polymorphism, (ii) a deletion, (iii) an insertion, (iv) a translocation, (v) a number of homologous chromosomes, (vi) a first deoxyribonucleic acid methylation pattern, and (vii) a presence of one or more alleles; and
inputting the extracted features into the machine-learning model to make a prediction of a phenotype of the individual.

11. The non-transitory computer-readable storage medium of claim 10, wherein the operation further comprises:
generating a set of training instances, wherein each training instance includes an image of a respective hand and indicates one or more genetic characteristics; and
training the machine-learning model using the set of training instances.

12. The non-transitory computer-readable storage medium of claim 11, wherein the operation further comprises:
extracting, from each respective image of a respective training instance, a plurality of features, wherein the plurality of features includes at least a first feature;
identifying a feature subset from the plurality of features for the machine-learning model using a feature-selection technique, wherein the feature subset excludes the first feature and wherein the feature subset includes a number of features that is at least two orders of magnitude smaller than a number of training instances in the set of training instances; and
training the machine-learning model to predict the genetic trait based on the feature subset.

13. The non-transitory computer-readable storage medium of claim 10, wherein the collection of features includes geometric characteristics of ridges, loops, whorls, or arches found in a handprint of the hand.

14. The non-transitory computer-readable storage medium of claim 10, wherein the operation further comprises:
comparing the prediction to a list that cross-references genetic traits to genetic disorders; and
diagnosing the individual as having a genetic disorder based on the comparison.

15. The non-transitory computer-readable storage medium of claim 10, wherein the operation further comprises:
diagnosing the individual as having an elevated risk of developing a disease based on the prediction.

16. A system for diagnosing a genetically based trait of an individual based on a hand, the system comprising:
one or more processors; and
a memory storing one or more applications that, when executed on the one or more processors, perform an operation, the operation comprising:
receiving a digital image of the hand created from scan data captured by a three-dimensional (3D) scanner, wherein the digital image is a three-dimensional (3D) model of the hand that captures a palm side of the hand and additional 3D aspects of the hand that extend beyond the palm side of the hand,
extracting, from the digital image via a processor applying at least one computer-vision technique for feature extraction, a collection of features characterizing three-dimensional (3D) aspects of the hand, wherein the collection of features includes directional variance of a ridge-orientation field;
inputting the extracted features into a machine-learning model executed by the processor to make a prediction of whether the individual has a genetic trait, wherein the machine-learning model is trained to predict the genetic trait based on the collection of features, and wherein the prediction includes predicting whether the individual has: (i) a first genotype, (ii) a single-nucleotide polymorphism, (ii) a deletion, (iii) an insertion, (iv) a translocation, (v) a number of homologous chromosomes, (vi) a first deoxyribonucleic acid methylation pattern, and (vii) a presence of one or more alleles; and
inputting the extracted features into the machine-learning model to make a prediction of a phenotype of the individual.

17. The system of claim 16, wherein the operation further comprises:
generating a set of training instances, wherein each training instance includes an image of a respective hand and indicates one or more genetic characteristics; and
training the machine-learning model using the set of training instances.

18. The system of claim 17, wherein the operation further comprises:
extracting, from each respective image of a respective training instance, a plurality of features, wherein the plurality of features includes at least a first feature;
identifying a feature subset from the plurality of features for the machine-learning model using a feature-selection technique, wherein the feature subset excludes the first feature and wherein the feature subset includes a number of features that is at least two orders of magnitude smaller than a number of training instances in the set of training instances; and training the machine-learning model to predict the genetic trait based on the feature subset.

19. The system of claim 16, wherein the collection of features includes geometric characteristics of ridges, loops, whorls, or arches found in a handprint of the hand.

20. The system of claim 16, wherein the operation further comprises:

comparing the prediction to a list that cross-references genetic traits to genetic disorders; and diagnosing the individual as having a genetic disorder based on the comparison.

* * * * *